(12) United States Patent
Deal

(10) Patent No.: US 9,585,989 B2
(45) Date of Patent: Mar. 7, 2017

(54) URETERAL STENT HAVING VARIABLE HARDNESS

(75) Inventor: Travis Deal, Freedom, IN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 942 days.

(21) Appl. No.: 11/842,410

(22) Filed: Aug. 21, 2007

(65) Prior Publication Data

US 2008/0071384 A1    Mar. 20, 2008

Related U.S. Application Data

(60) Provisional application No. 60/826,133, filed on Sep. 19, 2006.

(51) Int. Cl.
| | | |
|---|---|---|
| *A61F 2/04* | (2013.01) | |
| *A61L 31/14* | (2006.01) | |
| *A61L 31/04* | (2006.01) | |
| *A61M 27/00* | (2006.01) | |

(52) U.S. Cl.
CPC ............ *A61L 31/148* (2013.01); *A61F 2/04* (2013.01); *A61L 31/041* (2013.01); *A61M 27/008* (2013.01); *A61F 2002/048* (2013.01); *A61F 2210/0004* (2013.01); *A61F 2230/0069* (2013.01); *A61F 2250/003* (2013.01); *A61F 2250/0012* (2013.01); *A61F 2250/0018* (2013.01); *A61F 2250/0029* (2013.01); *A61F 2250/0031* (2013.01)

(58) Field of Classification Search
CPC ........................ A61F 2002/048; A61M 27/008
USPC ........ 623/23.66, 23.7, 1.38–1.39, 1.42, 1.45, 623/23.64–23.71; 604/8
See application file for complete search history.

(56) References Cited

U.S. PATENT DOCUMENTS

| | | | |
|---|---|---|---|
| 4,820,262 A | | 4/1989 | Finney |
| 4,874,360 A | * | 10/1989 | Goldberg ............ A61M 27/008 604/544 |
| 5,019,102 A | | 5/1991 | Hoene |
| 5,049,138 A | | 9/1991 | Chevalier et al. |
| 5,085,629 A | | 2/1992 | Goldberg et al. |
| 5,401,257 A | | 3/1995 | Chevalier, Jr. et al. |
| 5,464,450 A | | 11/1995 | Buscemi et al. |
| 5,500,013 A | | 3/1996 | Buscemi et al. |
| 5,599,291 A | * | 2/1997 | Balbierz et al. .................. 604/8 |
| 5,814,006 A | | 9/1998 | Planz |

(Continued)

FOREIGN PATENT DOCUMENTS

| | | |
|---|---|---|
| WO | WO 89/05127 | 6/1989 |
| WO | WO 94/25093 | 11/1994 |
| WO | WO 96/11721 | 4/1996 |

OTHER PUBLICATIONS

Wikipedia. "Superoxide dismutase". Downloaded from <http://en.wikipedia.org/wiki/Superoxide_dismutase> on Oct. 12, 2012.*

(Continued)

*Primary Examiner* — Andrew Iwamaye

(57) ABSTRACT

A ureteral stent includes a first material and a second material. The second material is formulated to have a hardness that is greater than a hardness of the first material. The second material is formulated to be soluble in a bodily fluid. The second material is combined with the first material to form a substantially homogeneous combination of the first material and the second material.

11 Claims, 8 Drawing Sheets

(56) References Cited

U.S. PATENT DOCUMENTS

| | | | |
|---|---|---|---|
| 5,964,744 | A | 10/1999 | Balbierz et al. |
| 6,160,084 | A | 12/2000 | Langer et al. |
| 6,228,111 | B1 | 5/2001 | Tormala et al. |
| 6,284,333 | B1 | 9/2001 | Wang et al. |
| 6,368,356 | B1 | 4/2002 | Zhong et al. |
| 6,387,124 | B1 | 5/2002 | Buscemi et al. |
| 6,620,202 | B2 | 9/2003 | Bottcher et al. |
| 6,676,624 | B2 | 1/2004 | Gellman |
| 6,709,465 | B2 | 3/2004 | Mitchell et al. |
| 6,719,804 | B2* | 4/2004 | St. Pierre ............ 623/23.7 |
| 6,887,215 | B2 | 5/2005 | McWeeney |
| 6,908,447 | B2 | 6/2005 | McWeeney et al. |
| 6,913,765 | B2 | 7/2005 | Li et al. |
| 7,169,178 | B1* | 1/2007 | Santos et al. ......... 623/1.42 |
| 7,288,084 | B2* | 10/2007 | Li ........................ 604/890.1 |
| 2001/0002411 | A1* | 5/2001 | Ronan ............ A61L 29/145 523/113 |
| 2003/0074082 | A1 | 4/2003 | Bottcher et al. |
| 2003/0153972 | A1* | 8/2003 | Helmus ................. 623/1.15 |
| 2003/0199993 | A1 | 10/2003 | Gellman et al. |
| 2003/0224033 | A1* | 12/2003 | Li et al. ................. 424/423 |
| 2004/0015187 | A1* | 1/2004 | Lendlein et al. ....... 606/228 |
| 2004/0022824 | A1* | 2/2004 | Li et al. ................. 424/423 |
| 2004/0044397 | A1* | 3/2004 | Stinson ................. 623/1.15 |
| 2004/0143209 | A1 | 7/2004 | Liu et al. |
| 2004/0249441 | A1* | 12/2004 | Miller et al. .......... 623/1.15 |
| 2005/0043783 | A1 | 2/2005 | Amis et al. |
| 2005/0085916 | A1* | 4/2005 | Li et al. ............... 623/17.16 |
| 2005/0209680 | A1* | 9/2005 | Gale et al. ............ 623/1.15 |
| 2005/0228481 | A1 | 10/2005 | Manasas et al. |
| 2006/0224237 | A1* | 10/2006 | Furst et al. ........... 623/1.46 |
| 2006/0229711 | A1* | 10/2006 | Yan et al. ............. 623/1.38 |
| 2006/0264912 | A1* | 11/2006 | McIntyre et al. .... 604/891.1 |
| 2007/0282431 | A1* | 12/2007 | Gale et al. ............ 623/1.38 |

OTHER PUBLICATIONS

Chemicalland21. "Triclosan" . Accessed at <http://www.chemicalland21.com/lifescience/phar/TRICLOSAN.htm> on Sep. 7, 2013.*
DuPont. "DuPont Packaging & Industrial Polymers: DuPont Elvax® 40W". Downloaded from <http://www.dupont.com/content/dam/assets/products-and-services/packaging-materials-solutions/assets/elvax_40w.pdf> on Nov. 25, 2014.*
Hercules Incorporated, Aqualon Division, "Klucel—Physical and Chemical Properties," 2001.
Dupont Company, "DuPont™ Elvax, EVA resins for Molding, Compounding, and Extrusion," [online] [retrieved on Sep. 9, 2005] Retrieved from the Internet <URL: http://www.dupont.com/indistrial-polymers/elvax/H-08772-2/H-08772-2.html>.
Boston Scientific, "Polaris™ Ureteral Stent, Ureteral Stent—Firm Placement, Soft Comfort, Boston Scientific," [online] [retrieved on Aug. 29, 2005] Retrieved from the Internet <URL: http://www.bostonscientific.com/med_specality/deviceDetail.jsp?task=tskBasicDevice.jsp . . . >.
Hercules Incorporated, "Klucel® Hydroxypropylcellulose (HPC)".
International Search Report for International Application No. PCT/US2007/076640, mailed Nov. 12, 2007.
International Search Report and Written Opinion for PCT/US2007/078849, 11 pages, mailed Jan. 22, 2008.
Office Action for U.S. Appl. No. 11/855,274, 20 pages, mailed Jan. 16, 2009.
Office Action for U.S. Appl. No. 11/855,274, 18 pages, mailed Jul. 14, 2009.

* cited by examiner (PRIOR TO INSERTION)

(TIME = T1)

(TIME ≥ T2)

URETERAL STENT HAVING VARIABLE HARDNESS

CROSS-REFERENCE TO RELATED APPLICATIONS

This application claims priority to U.S. Provisional Application Ser. No. 60/826,133, entitled "Ureteral Stent Having Variable Hardness," filed Sep. 19, 2006, which is incorporated herein by reference in its entirety.

BACKGROUND

The disclosed invention relates generally to a medical device and more particularly to a ureteral stent having a temporally variable hardness.

Ureteral stents are typically placed within a urinary tract of a patient such that one end portion of the ureteral stent is located in a kidney of the patient and the other end portion of the ureteral stent is located in either a bladder or a ureter of the patient. Some known ureteral stents include retention members configured to retain the ureteral stent in a desired position within the patient. Known ureteral stents are typically positioned within the urinary tract of the patient by placing a guidewire within the patient, sliding the ureteral stent on the guidewire, and then pushing the ureteral stent along the guidewire into a desired position using a push rod. After an appropriate period of time, the ureteral stent is removed from the patient, for example by pulling the ureteral stent from the urinary tract of the patient.

Known ureteral stents are designed to provide optimal functionality while minimizing patient discomfort. Some design features that provide improved comfort, however, may decrease functionality. For example, hard stents are known to be more resistant to deformation and easier to position within the urinary tract than soft stents. As the hardness of the stent increases, however, the patient will generally experience greater discomfort while the stent is within the urinary tract. Conversely, softer stents may alleviate patient discomfort, but they are generally more difficult to insert into the patient.

To accommodate the need for both comfort and functionality, some known ureteral stents are configured such the stent hardness (also characterized as the stent durometer) varies spatially along the longitudinal axis of the stent. For example, the distal end section has a relatively high durometer, facilitating insertion of the stent (for which the durometer of the distal end portion is more important) while the proximal end portion has a relatively low durometer, affording greater comfort to the patient because the proximal end portion is typically in contact with the more sensitive area at the junction of the ureter and bladder. Other known stents are configured such that all or a portion of the stent dissolves or degrades upon being inserted into the patient's urinary tract, thereby increasing patient comfort and eliminating the need to remove the stent. Such dissolvable stents, however, do not retain their original shape or size.

Thus, a need exists for a ureteral stent configured to have a relatively high durometer to ease insertion and that softens after insertion to increase patent comfort, while retaining its original size and/or shape.

SUMMARY

The disclosed ureteral stent has a first material and a second material. The second material is formulated to have a hardness that is greater than a hardness of the first material. The second material is formulated to be soluble in a bodily fluid. The second material is combined with the first material to form a substantially homogeneous combination of the first material and the second material.

DETAILED DESCRIPTION

Ureteral stents having a first material and a second material are disclosed herein. In some embodiments, the second material is formulated to have a hardness that is greater than a hardness of the first material. The second material is formulated to be soluble in a bodily fluid. The second material is combined with the first material to form a substantially homogeneous combination of the first material and the second material. In this manner, upon insertion into a patient, the second material dissolves, thereby causing a temporal change in the hardness of the stent.

In some embodiments, the shape of the ureteral stent does not change with the dissolution of the second material. In other embodiments, the size of the ureteral stent does not change with the dissolution of the second material.

In some embodiments, a medical device includes an elongate member having a side wall defining a lumen configured to convey a fluid within a body of a patient. The elongate member includes a distal end portion, a proximal end portion, and a medial portion disposed between the distal end portion and the proximal end portion. At least one of the distal end portion, the proximal end portion, and the medial portion includes a substantially homogeneous combination of materials including a first material and a second material, the second material being formulated to be soluble in a bodily fluid such that dissolution of the second material does not alter the size of the elongate member.

In some embodiments, a method includes blending a first material having a hardness and a second material having a hardness greater than the hardness of the first material to produce a substantially homogeneous combination of the first material and the second material. The blending can be performed, for example, by melt blending the first material and the second material. At least a portion of the second material is formulated to be soluble in a bodily fluid. A ureteral stent is formed from the substantially homogeneous combination of the first material and the second material.

The terms hardness, strength and/or resistance to deformation are used herein to denote a number of related properties associated with a ureteral stent. For example, the terms may be used to refer to specific material properties of the materials from which a ureteral stent is formed. Such material properties can include the yield strength, the modulus of elasticity, the modulus of rigidity, the hardness and/or the elongation percentage. The hardness of a material or stent may be characterized as its "durometer," in reference to the apparatus used to measure the hardness of the types of material often used to form ureteral stents.

Figure 1:
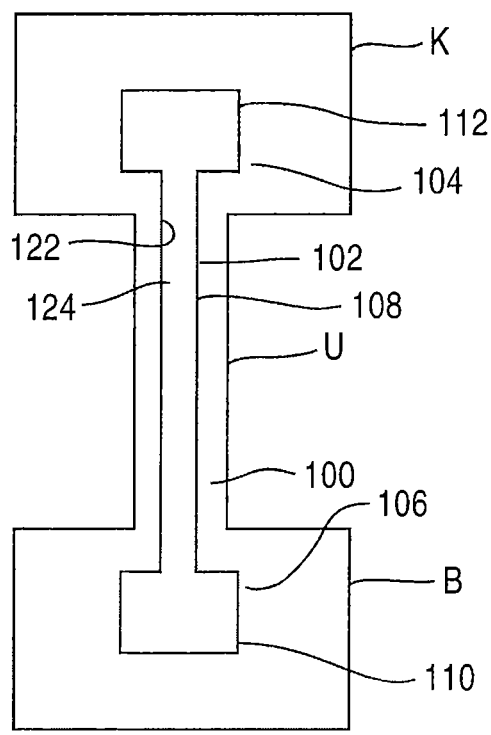
FIG. 1 is a schematic illustration of a ureteral stent according to an embodiment of the invention.

FIG. 1 is a schematic illustration of a ureteral stent 100 according to the invention that is disposed within a urinary tract of a patient. The ureteral stent 100 is positioned within a patient such that it extends from the kidney K, through the ureter U, and to the bladder B. The ureteral stent 100 is configured to facilitate the movement of fluid within a urinary tract of a patient, for example, from the kidney K to the bladder B via the ureter U.

The ureteral stent 100 includes an elongate member 102 having a distal end portion 104, a proximal end portion 106, and a medial portion 108 extending between the distal end portion 104 and the proximal end portion 106. The proximal end portion 106 includes a retention portion 110. Similarly, the distal end portion 104 includes a retention portion 112.

The retention portion 110 of the proximal end portion 106 of the ureteral stent 100 is configured to be placed within the bladder B to help prevent migration of the ureteral stent 100 upwardly (i.e., distally) toward the kidney K. Similarly, the retention portion 112 of the distal end portion 104 is configured to be placed within the kidney K to help prevent migration of the ureteral stent 100 downwardly (i.e., proximally) toward the bladder B. Accordingly, the retention portions 110 and 112 are configured to help retain the ureteral stent 100 in place within the urinary tract of the patient. The retention portions 110 and 112 may be configured in a variety of different shapes and sizes, such as a loop or a "J" hook. Although the ureteral stent 100 is illustrated and described as including retention portions 110 and 112, in some embodiments, one or both of the proximal end portion 106 and the distal end portion 104 do not include retention portions.

The ureteral stent 100 includes a side wall 122 that defines a lumen 124. The lumen 124 extends from the distal end portion 104 to the proximal end portion 106 of the ureteral stent 100. In some embodiments, the lumen only extends through a portion of the ureteral stent. In other embodiments, the ureteral stent does not include a side wall that defines a lumen.

Figure 2A:
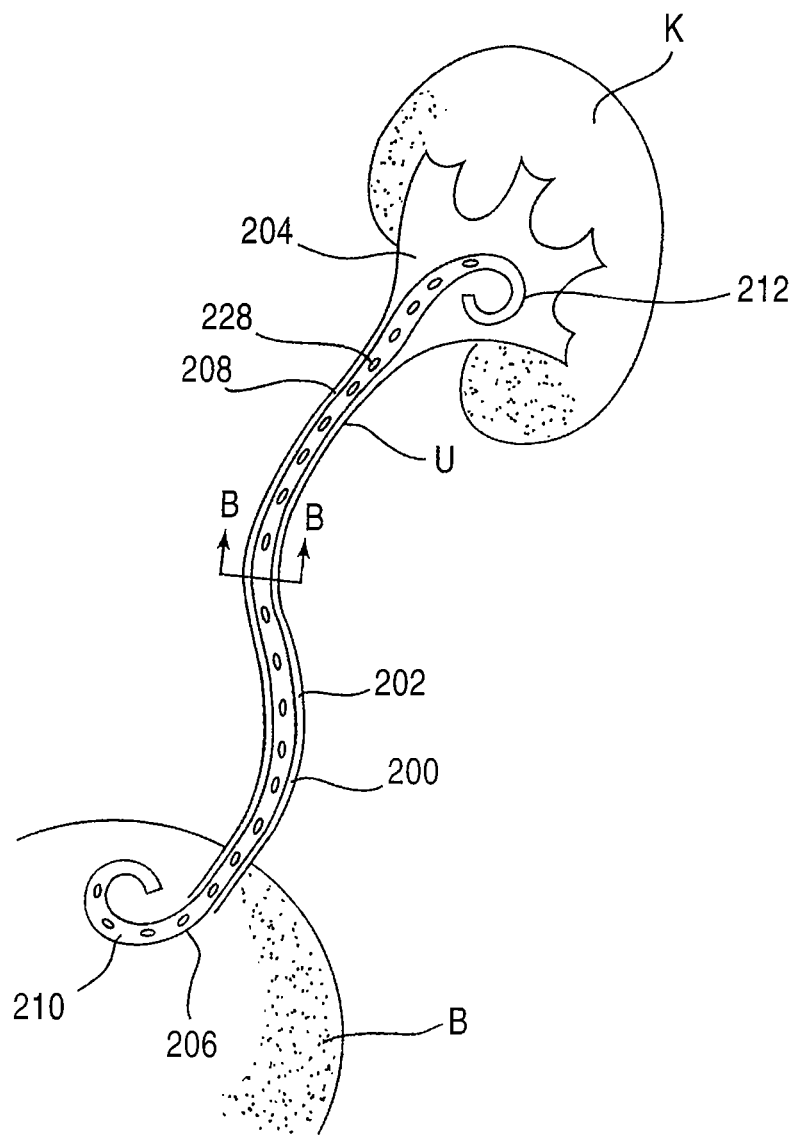
FIG. 2A illustrates a ureteral stent according to an embodiment of the invention disposed within the urinary tract of a patient.
Figure 2B:
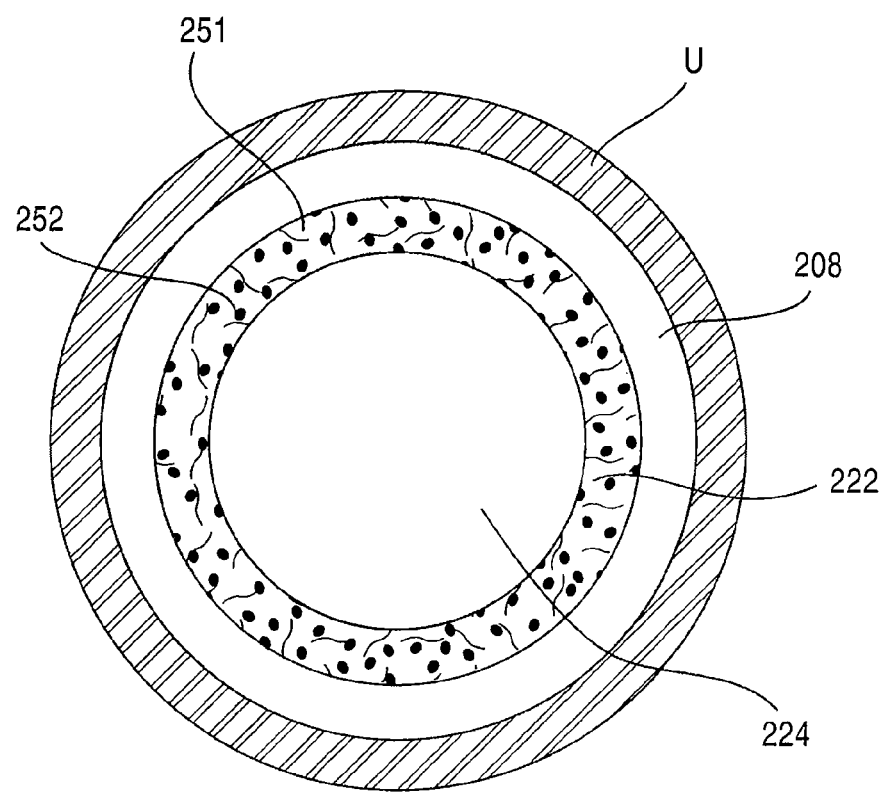
FIG. 2B is an enlarged cross-sectional view of a portion of the ureteral stent shown in FIG. 2A taken along line B-B in FIG. 2A.

FIGS. 2A and 2B show a ureteral stent 200 according to an embodiment of the invention that is positioned within a urinary tract of a patient. The ureteral stent 200 is positioned within a patient such that it extends from a kidney K, through a ureter U, and to a bladder B. The ureteral stent 200 includes an elongate member 202 having a distal end portion 204, a proximal end portion 206 and a medial portion 208 extending between the distal end portion 204 and the proximal end portion 206. The proximal end portion 206 includes a retention portion 210. Similarly, the distal end portion 204 includes a retention portion 212. The ureteral stent 200 also includes a side wall 222 that defines a lumen 224 extending from the distal end portion 204 to the proximal end portion 206 of the ureteral stent 200. In the illustrated embodiment, the ureteral stent 200 includes one or more side ports 228 that allow fluid to pass from the lumen 224 to a location outside of the ureteral stent 200.

As illustrated in FIG. 2B, the ureteral stent 200 is constructed from a substantially homogeneous mixture or combination of a first material 251 and a second material 252. The first material 251 is formulated to have a hardness less than that of the second material 252. The second material 252 is formulated to be soluble in a bodily fluid, such as, for example, water, urine, mucous and the like. In use, after the ureteral stent 200 is inserted into a patient, at least a portion of the harder second material 252 dissolves. In some embodiments, all of the second material 252 eventually dissolves, leaving only the softer first material 251. In this manner, the ureteral stent 200 can have a first hardness during the insertion process and second hardness less than the first hardness while residing within a patient, thereby improving patient comfort.

Figure 3A:
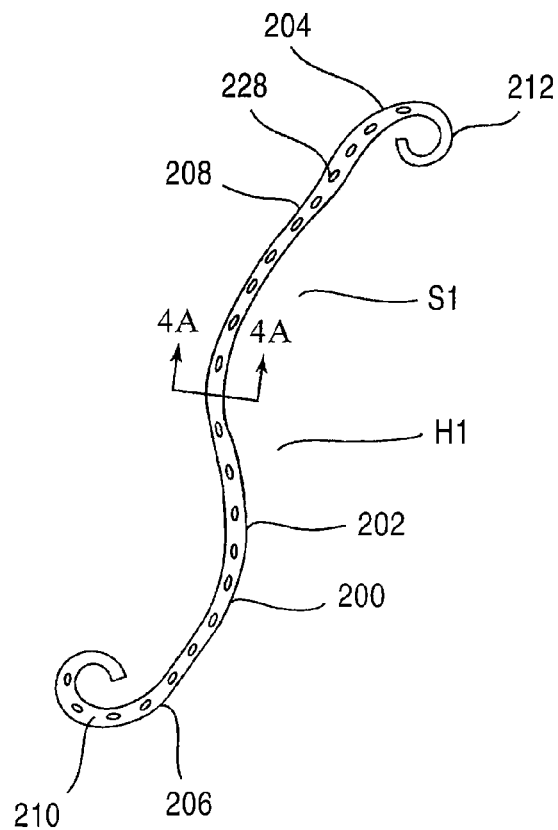
FIGS. 3A-3C illustrate the ureteral stent shown in FIG. 2A in three different configurations as a function of the time elapsed after insertion.
Figure 4A:
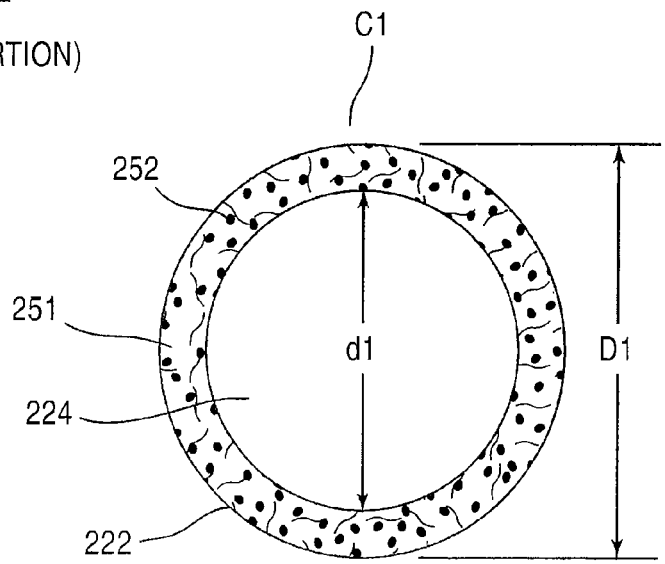
FIGS. 4A-4C are cross-sectional views of a portion of the ureteral stents shown in FIGS. 3A-3C, respectively, taken along lines 4A-4A, 4B-4B and 4C-4C, respectively.
Figure 3B:
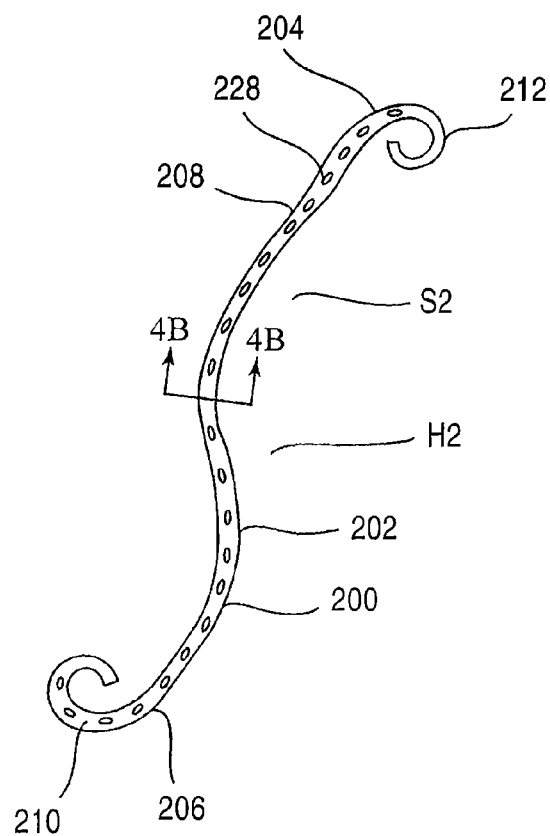
Figure 4B:
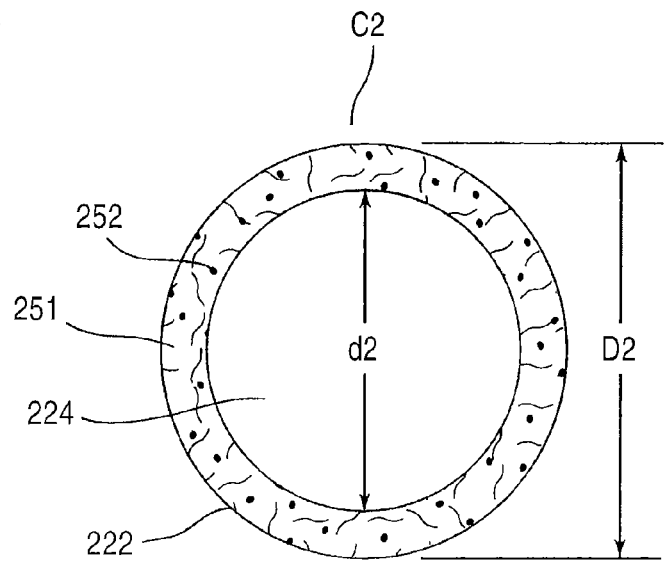
Figure 3C:
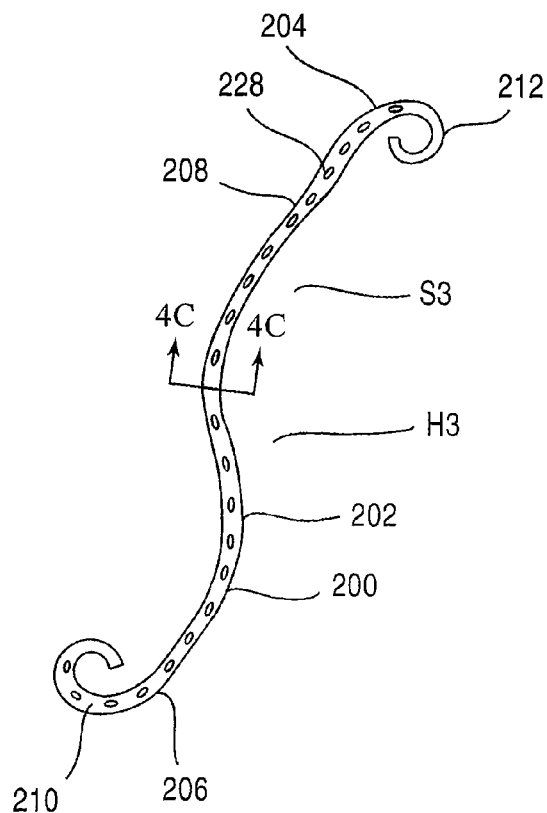
Figure 4C:
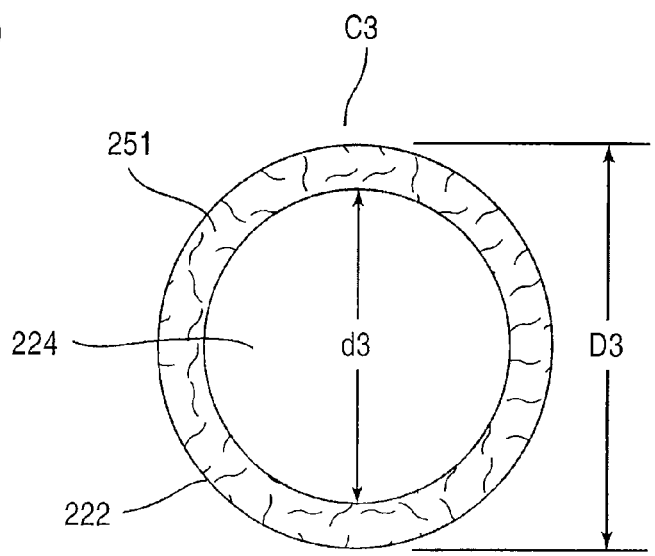

FIGS. 3A-3C depict the ureteral stent 200 at three different points in time to illustrate the temporal change in the structure of the ureteral stent 200 as a result of the dissolution of the second material 252. Similarly, FIGS. 4A-4C are cross-sectional views of the ureteral stent 200 illustrated in FIGS. 3A-3C. FIGS. 3A and 4A illustrate the ureteral stent 200 in an initial configuration, prior to being inserted into the body of a patient. As illustrated, the ureteral stent 200 is constructed from a substantially homogeneous combination of the first material 251 and the second material 252. The types of material used as well as the relative amounts of each material used will be discussed in more detail below. In the initial configuration, the ureteral stent 200 has a hardness of H1. Similarly, in the initial configuration, the ureteral stent 200 has an overall shape S1, a cross-sectional shape C1, a diameter d1 of the lumen 224, and an outer diameter D1 of the side wall 222.

FIGS. 3B and 4B illustrate the ureteral stent 200 in an intermediate configuration, after it has been inserted into the body of a patient and exposed to a bodily fluid for a specified time period T1. As illustrated, a portion of the second material 252 has dissolved due to the exposure of the ureteral stent 200 to a bodily fluid for the time period T1. The intermediate time period T1 can range from several minutes to several hours to several days, depending on the formulation of the second material 252. In the intermediate configuration, the hardness H2 of the ureteral stent 200 is less than the initial hardness H1. Moreover, in the intermediate configuration, the size and/or shape of the ureteral stent 200 remain unchanged from the initial size and shape. Said another way, the overall shape S2 is the same as the overall shape S1, the cross-sectional shape C2 is the same as the cross-sectional shape C1, the diameter d2 is the same as the diameter d1, and/or the outer diameter D2 is the same as the outer diameter D1.

FIGS. 3C and 4C illustrate the ureteral stent 200 in an final configuration, after it has been inserted into the body of a patient and exposed to a bodily fluid for at least a time period T2. As illustrated, the second material 252 has fully dissolved due to the exposure of the ureteral stent 200 to a bodily fluid for the time period T2. The final time period T2 can range from several minutes to several hours to several days, depending on the formulation of the second material 252. In some embodiments, the final time period T2 is approximately one to two hours. In the final configuration, the hardness H3 of the ureteral stent 200 is less than the initial hardness H1 and the intermediate hardness H2. In the final configuration, the overall shape S3 is the same as the overall shape S1, the cross-sectional shape C3 is the same as the cross-sectional shape C1, the diameter d3 is the same as the diameter d1, and the outer diameter D3 is the same as the outer diameter D1.

Although the ureteral stent 200 is shown and described as maintaining a constant size and shape as the second material 252 dissolves, in some embodiments, the size and/or shape may vary as a result of the dissolution of the second material 252. For example, in some embodiments, as the second material dissolves, the overall shape and cross-sectional shape remain constant while the diameter of the lumen and/or the outer diameter change. In other embodiments, as the second material dissolves, the overall shape and/or cross-sectional shape change while the diameter of the lumen and the outer diameter remain constant. In yet other embodiments, both the size and the shape of the ureteral stent change as the second material dissolves.

Figure 5A:
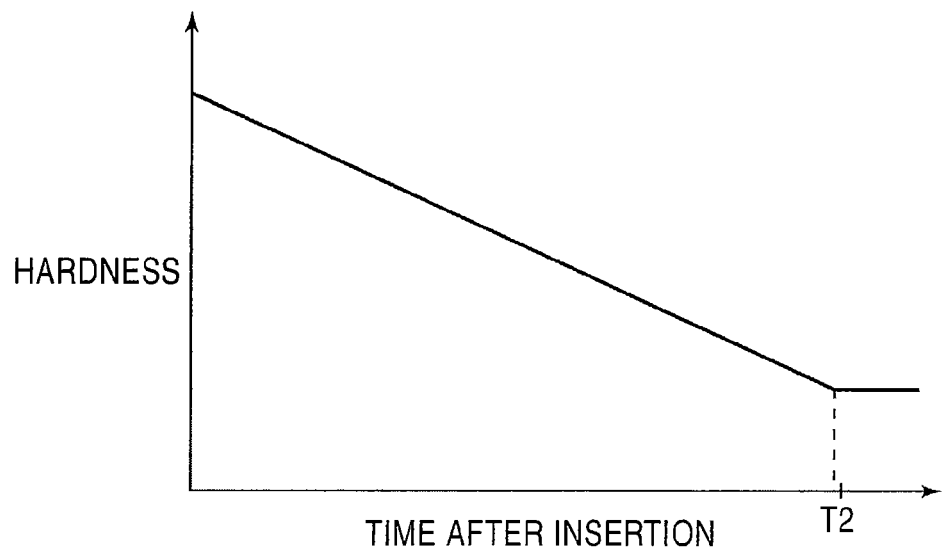
FIGS. 5A and 5B are plots showing the hardness and the material composition of the ureteral stent shown in FIG. 2A, respectively.
Figure 5B:
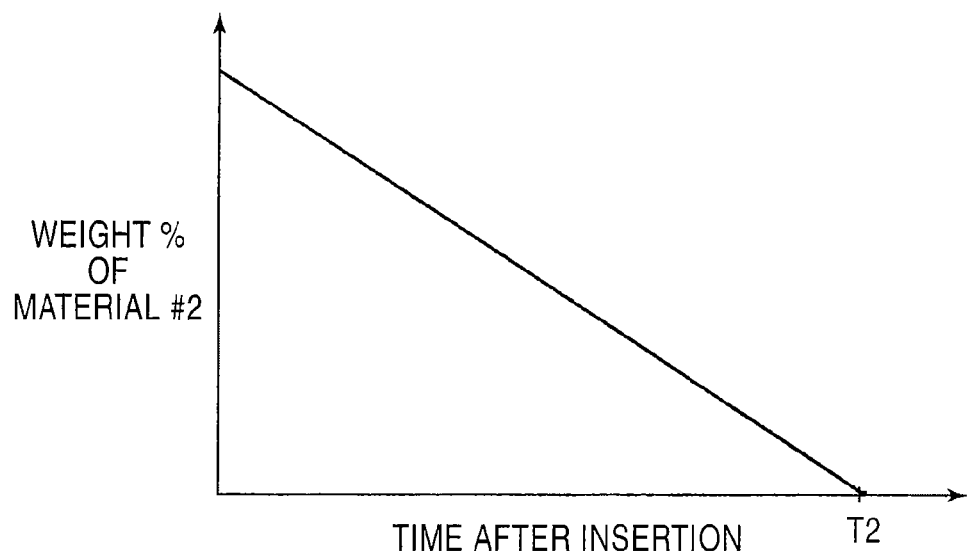

FIGS. 5A and 5B are plots showing the hardness and the weight percentage of the second material 252, respectively, of the ureteral stent 200 as a function of time after ureteral stent 200 is inserted into the body of a patient. As illustrated, the reduction in the hardness is related to the reduction in the weight percentage of the second material 252 resulting from the dissolution of the second material 252. Both the decrease in hardness and the reduction in weight percentage of the second material 252 occur at a substantially constant rate (as illustrated by the linear curves in FIGS. 5A and 5B) until the second material 252 is completely dissolved and the ureteral stent 200 is in its final configuration (at time T2). As will be discussed in more detail below, the amount of change in the hardness of the ureteral stent 200 is dependent on the formulation of the first material 251, the second material 252 and/or the initial weight percentage of the second material 252.

Figure 6A:
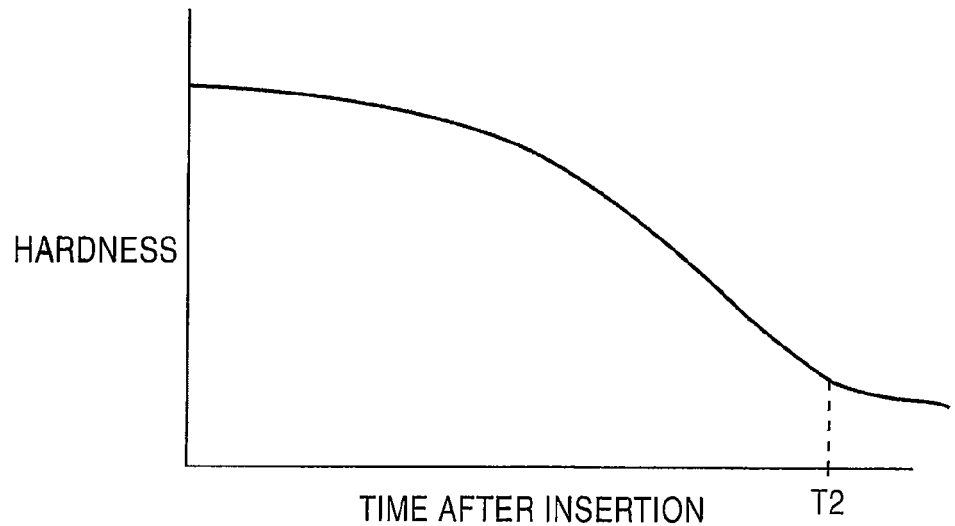
FIGS. 6A and 6B are plots showing the hardness and the material composition of a ureteral stent according to an embodiment of the invention, respectively.
Figure 6B:
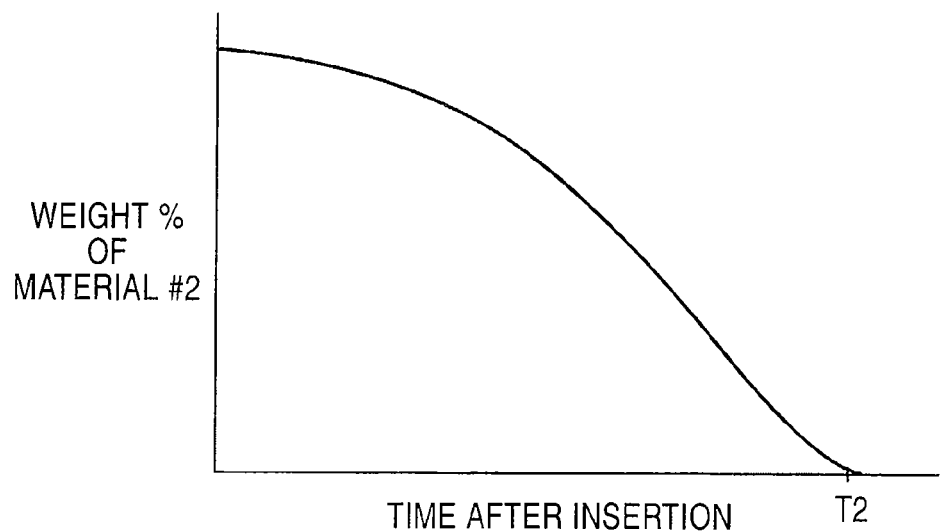

In some embodiments, the change in hardness and/or the reduction in weight percentage of the second material 252 occurs at a variable rate (resulting in a non-linear curve). For example, FIGS. 6A and 6B are plots similar to those illustrated in FIGS. 5A and 5B for a ureteral stent according to an embodiment of the invention. As described above, the ureteral stent includes a first material and a second material. As illustrated in FIGS. 6A and 6B, the ureteral stent is configured such that the second material dissolves at a variable rate (i.e., more slowly at first, then more rapidly). Similarly, the hardness of the ureteral stent decreases at variable rate. Such variable rates may be desirable to ensure that the ureteral stent remains sufficiently hard during the insertion process, but attains a lower, more comfortable level of hardness within a short period thereafter. The dissolution characteristics can be selected based on the formulation of the first material and/or the second material.

Although the ureteral stent 200 is shown and described as being constructed from a substantially homogeneous combination of a first material 251 and a second material 252, in some embodiments only a portion of the ureteral stent is constructed from two different materials. For example, in some embodiments, only the distal end, the proximal end and/or the medial portion are constructed from two materials. In this manner, a preselected portion of the ureteral stent will have a hardness that varies temporally upon insertion.

The first material 251 can be any material known in the art to be used in constructing ureteral stents. Such materials exhibit at least some of the following characteristics: high tensile strength, high retention coil strength, excellent biocompatibility and biodurability, excellent radiopacity or fluoroscopic visibility, and availability in varying durometers. In some embodiments the first material 251 is a biocompatible plastic, such as, for example ethylene vinyl acetate ("EVA"). In other embodiments, the first material 251 is EVA having a weight percentage of vinyl acetate ranging from nine percent to forty percent. In yet other embodiments, the first material 251 is EVA having a weight percentage of vinyl acetate of approximately twenty eight percent. In yet other embodiments, the first material 251 includes a radiopaque marker, such as bismuth.

Similarly, the second material 252 can be any material known in the art to be usable in constructing ureteral stents that is soluble in a bodily fluid, such as water, urine and/or mucous. Such materials include bioabsorbable polymers as disclosed in U.S. Pat. Nos. 5,464,450, 6,387,124, and 5,500,013, the disclosures of which are incorporated herein by reference in their entirety. In some embodiments, for example, the second material 252 can include poly-L-lactide, polyglycolic acid (PGA), polylactic acid, collagen, polycaprolactone, hylauric acid, polyethylene glycol, polyvinylpyrrolidone, polyvinylpyrrolidone, high molecular weight carbohydrates and/or any combination thereof. In some embodiments, the second material 252 can be a biocompatible plastic, such as, for example, hydroxypropylcellulose. In other embodiments, the second material 252 is hydroxypropylcellulose having an average molecular weight of at least 80,000. In yet other embodiments, the second material 252 is hydroxypropylcellulose having an average molecular weight of approximately 80,000.

The relative amount of the second material can be varied depending on the desired properties of the ureteral stent. For example, in some embodiments, the initial weight percentage of the second material can be as low as ten percent. In such embodiments, since only a small portion (i.e., ten percent by weight) of the overall material dissolves, the hardness, strength, and/or resistance to deformation of the ureteral stent may not undergo a significant temporal change after being inserted into a patient's body. In other embodiments, the initial weight percentage of the second material can be as high as eighty percent. In such embodiments, the hardness, strength, and/or resistance to deformation of the ureteral stent may significantly change after being inserted into a patient's body. In yet other embodiments, the ratio of materials can vary spatially. In this manner, selected portions of the ureteral stent can be configured to change significantly after insertion, while other portions of the ureteral stent can be configured to remain relatively unchanged.

The first material and the second material can be combined in a number of different ways to achieve a substantially homogenous combination. In some embodiments, for example, the two materials are melt blended in a two-step process. The first step includes independently melting and extruding each of the materials. In this manner, each material is transformed from its initial state, which can be that of a powder, a pellet, or the like, into a similar extruded structure. The extruded structures are then divided into smaller portions. The smaller portions of each material are then combined in the desired ratio and melted together. Finally, the combined material is extruded to form the ureteral stent. In this manner, the melt blending is controlled to ensure that the two materials are combined to form a substantially homogeneous combination.

In some embodiments, the selected first material and second material are combined with a third material, which acts as a bonding agent to ensure that the first material and the second material are sufficiently bonded together. In other embodiments, the materials are combined without a bonding agent.

While various embodiments of the invention have been described above, it should be understood that they have been presented by way of example only, and not limitation. For example, while the invention is shown and described as including a ureteral stent, in other embodiments the invention may include any medical device configured to convey a fluid within the body of a patient, such as, for example, a ureteral catheter.

While the ureteral stents shown and described above as including a substantially homogeneous combination of a first material and a second material, in some embodiments, a ureteral stent can be constructed from a single material formulated such that upon contact with a bodily fluid the hardness of the ureteral stent decreases, while the size and the shape of the ureteral stent remain substantially unchanged.

While the ureteral stents shown and described above as including a first material and a second material formulated to have a hardness that is greater than a hardness of the first material, in some embodiments, a ureteral stent can be constructed from a first material and a second material formulated to have a hardness less than a hardness of the first material. In other embodiments, a ureteral stent can be constructed from a first material and a second material formulated to have different material properties than the first material. Such material properties can include, for example, the yield strength, the modulus of elasticity, the modulus of rigidity, the lubricity and/or the elongation percentage. In yet other embodiments, a ureteral stent can be constructed from a first material and a second material configured to have different geometric characteristics, such as a stress concentration riser, than the first material.

While the ureteral stents shown and described above as being constructed from a substantially homogeneous combination of a first material and a second material, in some embodiments, a ureteral stent can be constructed from a non-homogeneous combination of a first material and a second material.

What is claimed is:

1. A non-drug-eluting ureteral stent, comprising:
an elongate portion having an inner surface defining a lumen and an outer surface configured to contact a portion of a body, the elongate portion having a plurality of side ports defined therein, a side port of the plurality of side ports defining an opening from the outer surface to the lumen, the elongate portion having a first retention portion configured to be placed within a bladder of a patient and a second retention portion configured to be placed within a kidney of the patient, the first retention portion being disposed in a first orientation with respect to a longitudinal axis of a medial portion of the elongate portion, the second retention portion being disposed in a second orientation with respect to the longitudinal axis, the second orientation being different than the first orientation, the second retention portion being constructed from a first material and a second material combined with the first material to form a composite of the first material and the second material, the first retention portion being constructed from the first material and being devoid of the second material, a concentration of the second material in the composite of the first material and the second material varying along a length of the elongate portion,
the first material being formulated to be insoluble in a bodily fluid, the second material being formulated to be soluble in the bodily fluid,
the first material having a first hardness, and the second material has a second hardness that is greater than the first hardness,
the first material including a radiopaque material,
the second material, when in contact with the bodily fluid, will dissolve in one hour, such that a hardness of the second retention portion decreases while a size and a shape of the second retention portion remain unchanged, and
a dissolution rate of the second material as a function of a time in contact with the bodily fluid is constant.

2. The non-drug-eluting ureteral stent of claim 1, wherein a shape of the ureteral stent does not change with dissolution of the second material.

3. The non-drug-eluting ureteral stent of claim 1, wherein the lumen defines an inner diameter and the outer surface circumscribes the lumen and defines an outer diameter, the inner diameter and the outer diameter remaining constant with a dissolution of the second material.

4. The non-drug-eluting ureteral stent of claim 1, wherein the first material includes ethylene vinyl acetate having a weight percentage of vinyl acetate ranging from nine percent to forty percent.

5. The non-drug-eluting ureteral stent of claim 1, wherein a weight percentage of the second material prior to contact with the bodily fluid is between ten percent and eighty percent.

6. The non-drug-eluting ureteral stent of claim 1, wherein the first material includes a plastic and the second material includes at least one of a synthetic polymer, a plastic, and a hydroxypropylcellulose.

7. A non-drug-eluting medical device, comprising:
an elongate member having a side wall having an inner surface defining a lumen configured to convey a fluid within a body of a patient, the side wall having an outer surface configured to contact a portion of the body, the inner surface defining an inner diameter of the elongate member, the outer surface defining an outer diameter of the elongate member, the elongate member having a plurality of side ports defined therein, a side port of the plurality of side ports defining an opening from the outer surface to the lumen, the elongate member including a distal end portion having a first retention member and being configured to be placed within a kidney of the patient, a proximal end portion having a second retention member and being configured to be placed within a bladder of the patient, and a medial portion disposed between the distal end portion and the proximal end portion, the first retention member being disposed in a first orientation with respect to a longitudinal axis of the medial portion, the second retention member being disposed in a second orientation with respect to the longitudinal axis, the second orientation being different than the first orientation,
the medial portion and the distal end portion including a composite material including a combination of a first material and a second material from the inner surface to the outer surface, a concentration of the second material in the composite material varying along a length of the medial portion and the distal end portion of the elongate member, the proximal end portion including the first material and being devoid of the second material, the second material being formulated to be soluble in a bodily fluid such that dissolution of the second material does not alter the inner and outer diameter of at least one of, and the distal end portion of the elongate member, the second material having a hardness greater than a hardness of the first material,
the medial and distal end portions of the elongate member having a resistance to deformation, the dissolution of the second material does not alter a shape of the at least one of end portion, the medial portion and the distal end portion, and the dissolution of the second material causing a decrease in the resistance to deformation of the medial and distal end portions of the elongate member.

8. The non-drug-eluting medical device of claim 7, wherein the composite material is a melt blend of the first material and the second material.

9. The non-drug-eluting medical device of claim 7, wherein dissolution of the second material does not alter a cross-sectional area of the at least one of the proximal end portion, the medial portion, and the distal end portion of the elongate member.

10. The non-drug-eluting medical device of claim 7, wherein the second material includes at least one of a synthetic polymer, a plastic, and a hydroxypropylcellulose.

11. A non-drug-eluting ureteral stent, comprising:

an elongate member having a first retention portion configured to be disposed within a bladder of a patient and a second retention portion configured to be disposed within a kidney of the patient, the first retention portion being disposed in a first orientation with respect to a longitudinal axis of a medial portion of the elongate member, the second retention portion being disposed in a second orientation with respect to the longitudinal axis, the second orientation being different than the first orientation, the elongate member having a plurality of side ports defined therein, a side port of the plurality of side ports defining an opening in the elongate member, a portion of the elongate member including the second retention portion having a hardness, a size, and a shape, the portion of the elongate member being constructed from a composite material including a combination of a first material formulated to be insoluble in a bodily fluid and a second material formulated to be soluble in the bodily fluid such that upon contact with the bodily fluid the hardness of the portion of the elongate member decreases, while the size and shape of the portion of the elongate member remain unchanged, the second material including a plastic, the first retention portion being constructed of the first material and being devoid of the second material, a concentration of the second material in the composite material varying along a length of the portion of the elongate member, the first material having a hardness less than a hardness of the second material, the elongate member having an inner surface defining a lumen configured to convey a fluid within a body of the patient and an outer surface configured to contact a portion of the body, the inner surface defining an inner diameter of the lumen, the outer surface defining an outer diameter of the elongate member, and the composite material being formulated such that dissolution of the second material does not alter the outer diameter of the elongate member and the inner diameter of the lumen.

\* \* \* \* \*